(12) United States Patent
Holeczek et al.

(10) Patent No.: US 8,902,427 B2
(45) Date of Patent: Dec. 2, 2014

(54) SYSTEM FOR MEASURING PROPERTIES OF TEST SAMPLES IN FLUID

(75) Inventors: Michael Holeczek, Weilheim (DE); Heike Seibt, Weilheim (DE); Ulrich Rettig, Wielenbach (DE); Amir Agah, Weilheim (DE); Marlene Holderried, Schongau (DE); Thomas Benz, Weilheim (DE)

(73) Assignee: WTW Wissenschaflich-Technische Werstatten GmbH, Weilheim (DE)

( * ) Notice: Subject to any disclaimer, the term of this patent is extended or adjusted under 35 U.S.C. 154(b) by 66 days.

(21) Appl. No.: 13/467,350

(22) Filed: May 9, 2012

(65) Prior Publication Data

US 2012/0287422 A1 Nov. 15, 2012

(30) Foreign Application Priority Data

May 9, 2011 (DE) .......................... 10 2011 075 530

(51) Int. Cl.
*G01N 21/00* (2006.01)
*G01N 21/85* (2006.01)
*G01N 21/15* (2006.01)

(52) U.S. Cl.
CPC ...... *G01N 21/8507* (2013.01); *G01N 2021/154* (2013.01)
USPC ........................................................ 356/436

(58) Field of Classification Search
USPC .......................... 356/320, 338, 440; 73/61.69
See application file for complete search history.

(56) References Cited

U.S. PATENT DOCUMENTS

| 3,853,407 A | * | 12/1974 | Dewey, Jr. ................... 356/320 |
| 4,061,918 A |   | 12/1977 | Preier et al. |
| 4,313,340 A | * | 2/1982  | Schniewind ................. 73/61.69 |
| 5,334,536 A |   | 8/1994  | Nonnenmacher |
| 6,111,636 A |   | 8/2000  | Tuunanen |
| 2002/0167664 A1 | * | 11/2002 | Rettig et al. ................. 356/338 |
| 2005/0117156 A1 |   | 6/2005  | Siepmann et al. |
| 2012/0038925 A1 | * | 2/2012  | Gahr et al. ................... 356/440 |

FOREIGN PATENT DOCUMENTS

| DE | 2420060 | 11/1974 |
| DE | 6000002438294 | 2/1976 |
| DE | 141949 | 5/1980 |
| DE | 3839561 A1 * | 5/1990 |

(Continued)

OTHER PUBLICATIONS

German Search Report for German priority No. 10 2011 075 530.6, May 12, 2011.

(Continued)

*Primary Examiner* — Tarifur Chowdhury
*Assistant Examiner* — Jamil Ahmed
(74) *Attorney, Agent, or Firm* — RatnerPrestia (57) ABSTRACT

A photometer for measuring photometric magnitudes in a liquid medium includes a housing adapted to be introduced into the medium for on-site measurements; and light-emitting measuring beam transmitter and receiver that are arranged behind opposing measuring windows in a measuring slot in the housing, in which the slot is open to the medium. A measuring beam is generated in a measuring conduit in the measuring slot. A reference conduit is included for a reference measurement which is separate from the measuring conduit. At least one carrier part for the measuring beam transmitter and the measuring beam receiver is provided to move on a given path in the housing. The carrier part is constructed to move on the given path from the measuring conduit to the reference conduit and back, for measuring intensity values of the measuring beam in the measuring conduit and in the reference conduit.

16 Claims, 4 Drawing Sheets

(56) References Cited

FOREIGN PATENT DOCUMENTS

| DE | 4119346 | 12/1992 |
| --- | --- | --- |
| DE | 3839561 | 10/1996 |
| DE | 19811876 | 9/1999 |
| DE | 699 37 618 | 11/2008 |
| DE | 10 2007 029 536 | 1/2009 |
| DE | 10 2009 028 254 | 10/2010 |
| EP | 1472521 | 10/2006 |
| WO | WO8303900 | 11/1983 |

OTHER PUBLICATIONS

German Search Report for German priority No. 10 2011 075 530.6 (filed May 9, 2011) with English Translation, report issued on Aug. 22, 2012.

* cited by examiner

SYSTEM FOR MEASURING PROPERTIES OF TEST SAMPLES IN FLUID

CROSS REFERENCE TO RELATED APPLICATIONS

This application claims priority to German Patent Application No. 10 2011 075 530.6, filed May 9, 2011, the contents of such application incorporated by reference herein in its entirety.

FIELD OF THE INVENTION

The present invention relates to a photometer for measuring photometric magnitudes in fluids, in particular for the determination of constituents and concentrations of substances in liquid media. The invention relates to such photometers that are adapted for an on-site measuring in liquid media, i.e., with which a measurement can be carried out on site. Such photometers are used, for example, for the determination of constituents in drinking water, sea water, or in wastewater. The sound of the photometer is completely immersed into the water or into the aqueous solution and constituents such as, for example, the nitrate content of the water are measured by optical or electrochemical apparatuses.

BACKGROUND OF THE INVENTION

During the examination of various media (fluids) such as gases or aqueous solutions in the past, samples had to be taken and transported to a laboratory so that the analysis of the content of the samples could be carried out there. The sample taken had to be transported to the extent possible without change to its composition. The results of the analysis were only available at a later point in time. Furthermore, the analysis of liquid media in the laboratory has the disadvantage that a continuous monitoring of measuring magnitudes on site is not possible. Therefore, the present invention relates to such photometers and measuring sounds that are used especially for measuring on site in the medium itself. These measurements are also designated on-site measurements.

Various such photometers are known in the prior art that makes use of optical systems for the analysis of the liquid medium. As a rule, such traditional photometers have a transmitter and a receiver that produce a measuring beam over a measuring stretch so that the absorption of light in the medium can be measured. The measuring beam transmitter and the measuring beam receiver are received in a closed housing and provided with transparent windows in order that the measuring beam can be guided into the medium to be examined. The previously used systems of such photometers based on optical measuring differ on the one hand in the wavelength range of the measuring beam used. For example, DE 38 39 561 C1 discloses a photometer measuring apparatus with a liquid-tightly encapsulated immersion sound that transmits a measuring beam through opposing windows out of the housing through the medium using UV light. This known photometer uses two different measuring wavelengths, whereby an apparatus for breaking down the UV light into, on the one hand, a measured value wavelength and, on the other hand, a reference value wavelength is provided. The proportion of particles of the substance to be examined in the liquid can be determined from a comparison of the two wavelengths, on the one hand, of the measured value and, on the other hand, of the reference. Here, for example, a grid is used as the means for breaking down the single measuring beam of UV light into, on the one hand, the measured value wavelength and, on the other hand, the reference value wavelength, so that the UV light beam is spectrally divided. The detection of the two wavelengths then takes place by separate detectors.

Other photometers known in the prior art use a division of the measuring beam into two different beam paths for the measuring of photometric magnitudes. This takes place in DE 33 24 606 A by filters. In DE 44 07 332 C2 the splitting of the beam paths is carried out by fiber-optical light guides. In the known device from AT 408 488 B a measuring beam produced by a light source is again specially bundled by an optical lens so that the beam can be divided, on the one hand, into a measuring beam and, on the other hand, into a reference beam. The measuring beam is conducted through windows into a measuring slot in which the medium to be examined is located. The reference beam is conducted in the interior of the housing of the photometer. The detection of, on the one hand, the measuring beam and of, on the other hand, the reference beam is realized here by a beam selector in the form of a rotating disk with perforations, so that the intensities of the reference beam and the measuring beam can be detected at different points in time. An evaluation based on a comparison between the reference beam and the measuring beam also takes place here.

Referencing of the measurement, for example, by a separately running reference beam is necessary in such photometers in order to compensate a change of the optical devices due to the aging of components. If such photometers are used on site in a liquid for a rather long time period, it can occur that the measuring parameters change based on aging phenomena. Therefore, the measuring beam emitted by the measuring beam transmitter is conducted from time to time over a reference path in which a known and stable absorption prevails. Such photometers or spectrometers are checked with reference elements that are held in the measuring beam instead of measuring samples. This is not possible in the on-site photometers concerned in the present invention. For this reason the above-described systems were developed that either operate with different wavelengths or with splitting of the beam path of the measuring beam and with usage of different detectors for the split beam.

The present invention has the task of making a photometer for on-site measurements available that allows measurements over a larger wavelength range with the simplest means possible and that also allows long-term measurements in particular in liquid media on account of the quality of its reference.

This task is solved with a photometer with the features described below, having various advantageous embodiments.

SUMMARY OF THE INVENTION

The photometer in accordance with an embodiment of the present invention has a housing that is adapted to be introduced into a medium to be analyzed for measuring on site (or "in situ"), has a measuring beam transmitter for emitting light of at least one predetermined wavelength and has a measuring beam receiver that is adapted for receiving the light from the transmitter. The measuring beam transmitter and the measuring beam receiver are each built into the housing behind two opposite measuring windows that are present on a measuring slot in the housing in which the slot is open to the medium to be examined. In order to measure the photometric magnitude, in particular of a substance in the medium, a measuring beam is produced in a measuring conduit in the measuring slot and the light absorption and/or the light intensity of the measuring beam is measured. The photometer, in accordance with the invention, is characterized in that a reference channel separated from the measuring channel is present for a reference measurement and at least one carrier part can be moved in the housing of the photometer on a given path (B) for the measuring beam transmitter, the measuring beam receiver and/or optical structural components of the measuring beam transmitter or measuring beam receiver. The carrier part is constructed in the housing in such a manner that it can be moved on the given path from the measuring conduit into the reference conduit and back for measuring particular intensity values of the measuring beam in the measuring conduit and in the reference conduit, and means are provided for detecting and evaluating the intensity values measured.

In this manner a measuring beam can be shifted or moved inside the closed housing of the photometer from, on the one hand, the measuring conduit into, on the other hand, a position in which the measuring beam runs through a reference conduit inside the housing. The deflection of the measuring beam takes place, in accordance with the invention, by a shifting of the carrier part inside the housing of the photometer. The shifting of the carrier part takes place on a previously determined, defined path (B), so that the positional accuracy and zero point tracking of the measuring beam is possible, in spite of using the same transmitter elements and receiver elements. In this manner, the photometer can also be used in any wavelength ranges so that variability in the measuring of different substances, etc. is distinctly increased. On the other hand, no expensive electronic or mechanical division of the measuring beam into a reference component and a measuring component is necessary. The electronic or optical means necessary for this in the prior art can be eliminated. Furthermore, the spatial distance between the measuring conduit and the reference conduit can be selected to be relatively large by a shifting of the position of the measuring beam into, on the one hand, a measuring position (along a measuring conduit) and, on the other hand, the position of a reference conduit. An advantage of this is that the possible disturbances between a reference beam and a measuring beam are reduced. The distance between the measuring conduit and the reference conduit is preferably so great, according to the invention, that suitable optical sealing means, cameras, etc. can be readily housed. In this manner, the photometer, in accordance with the invention, makes possible a relatively high dynamic range and optical cross-talk or disturbance of the measurements is reduced on account of the separated reference conduit. Furthermore, the photometer of the invention has the advantage that the number of necessary components inside the housing is reduced. No different receiving elements or sensors for the reference measurement and the actual measurement in the medium are required. Last, but not least, the photometer in accordance with the invention, ensures a long-term and accurate measurement of photometric magnitudes over a much greater wavelength range than in the prior art. The wavelengths of the measuring beam can be adjusted as desired, in accordance with the absorption strength of the substance to be examined. For example, the photometer, in accordance with the invention, is especially suited for determining substances such as nitrate, nitrite, or other organic compounds in water, or in an aqueous solution.

According to an advantageous embodiment of the invention, the measuring beam transmitter and the measuring beam receiver are mounted on a common carrier part in the housing that can be moved on a linear path (B) for adjusting the measuring beam. The deflection, in accordance with the invention, of the measuring beam inside the housing of the photometer, therefore, takes place in a type of parallel shifting. The measuring beam transmitter and the measuring beam receiver are shifted in common with the structural carrier part carrying them. The relative position of transmitter to receiver is, therefore, securely ensured, and the shifting of the carrier part can be realized with comparatively simple means.

According to another advantageous embodiment of the invention the measuring beam of the photometer can be adjusted on a given circular path (B) between the measuring conduit and the reference conduit. A given circular path (B) of the measuring beam can be realized, for example, by a rotation of one or more of the carrier parts inside the housing. The deflection of the measuring beam onto a circular path has the advantage that it can be smoothly integrated into a circular tubular element of the photometer as an encapsulated housing. In addition, the circular path is simpler, more space-saving and can be executed with lower tolerances in the positioning of the structural components participating in the measurement in comparison to the straight-line shifting of the measuring beam.

According to another advantageous embodiment of the invention, the measuring conduit and the reference conduit have substantially the same geometry, in particular the same cross section and/or approximately the same length. The control and shifting of the measuring beam can, therefore, be carried out in a relatively simple manner with the same components in measuring light intensities in the measuring conduit, as well as measuring in the reference conduit. In particular, the zero point tracking and the beam production can be carried out with identical components.

According to another advantageous embodiment of the invention, the measuring of the intensity values is realized, on the one hand, in the measuring conduit and, on the other hand, in the reference conduit with identical parameters and/or components. Therefore, when measuring a certain substance content in the liquid, one and the same settings of the photometer are used for the referencing, on the one hand, and for the measuring, on the other hand. When measuring different substances with different absorption behavior, the particular required wavelength of the measurement can, of course, be appropriately set.

According to another advantageous embodiment of the invention, the cross section of the measuring beam of the photometer is smaller than the cross section of the measuring conduit and the reference conduit. In other words, the cross section of the measuring beam is adjusted to a diameter that is smaller than the cross section the measuring conduit and the reference conduit through which the measuring beam is conducted, as a function of the setting of the movable carrier part. The cross section of the measuring beam can preferably be set to ¾ the size of the conduit cross sections. According to the invention, diaphragms and lenses can preferably be used in the area of the measuring beam transmitter for the adjustment of the cross-sectional size of the measuring beam. The measuring beam can also be directly focused in the measuring beam transmitter and adjusted to a smaller cross section than that of the two conduits. This has the advantage that a high reproducibility can be achieved in the positioning of the measuring beam with the photometer. Moreover, reflections and deviations are reduced on the inner walls in the measuring conduit and/or in the reference conduit that could have a negative influence on the taking of the measured values and/or the intensity values. On the whole, this makes a more precise and more reliable measurement possible.

According to another advantageous embodiment of the invention, the measuring beam transmitter of the photometer is mounted on a first carrier part and the measuring beam receiver is mounted on a second carrier part and both carrier parts are rigidly connected to a shaft that is mounted to rotate about an axis of rotation inside the housing. The measuring beam receiver, as well as the measuring beam transmitter of the photometer can, therefore, be adjusted on a circular path, (for example, a semicircle) inside the housing. The relative position of the measuring beam receiver and the measuring beam transmitter is not influenced by this, since both are coupled to one another by a shaft rigidly connected to the carrier parts for the exact measurement. This has the advantage that a precise deflection of the measuring beam can be realized in a relatively small construction size. The rotating adjustment of the structural components relevant for the production of the measuring beam, can be affected by a single actuator. The rotational adjustment of the rotatable shaft can take place, for example, through 180°, so that the position of the measuring conduit, is furthest removed from that of the reference conduit so that the smallest or no possible influence of the particular measurements is given.

According to another advantageous embodiment of the invention, the measuring beam transmitter is mounted on a carrier part that is rigidly connected to a shaft that can rotate around an axis of rotation and the measuring beam receiver is arranged with its central axis in the axis of rotation of this shaft, whereby means are provided for deflecting the measuring beam in the direction toward the measuring beam receiver. As a result, the measuring beam receiver and the optical structural components belonging to the measuring beam receiver do not have to be moved in the interior of the housing of the photometer. The rigid positioning of the measuring beam receiver in the axis of rotation has the advantage that the measuring accuracy is further increased. A deflection of the measuring beam out of the axis of the measuring conduit and/or out of the reference conduit can take place, for example, by simple mirrors.

According to another advantageous embodiment of the invention, the measuring beam transmitter as well as the measuring beam receiver are arranged with their central axis in the axis of rotation of a rotatable shaft that is rigidly connected to at least one carrier part comprising optical means for the deflection of the measuring beam. The structural components of the measuring beam transmitter and the measuring beam receiver are, therefore, permanently mounted in the interior of the housing. A change of the measuring beam to a given path (B), (in the present case a circular path) takes place exclusively by rotating the at least one carrier part, that comprises appropriately adapted optical deflection elements. This embodiment has the advantage that the sensitive optical elements of the photometer are realized as immovable structural components. Nevertheless, a relatively large shift between the reference channel and the measuring channel is made possible, so that the advantages of the invention in variability of the measurements, allows a relatively simple construction and a high operating safety margin.

According to another advantageous embodiment of the invention, the carrier part in the photometer housing has a substantially U-shaped form whose inner dimensions are adapted for receiving the measuring slot of the housing, in which the slot is open to the medium. The U-shaped form of the carrier part, that carries the measuring beam transmitter, as well as the measuring beam receiver in one piece, has the advantage that a very robust support and hold is ensured for the structural components critical for the measurement. The adjusting of the position of the measuring beam from the reference conduit into the measuring conduit can take place by a transversal movement of the carrier part, or by a rotary adjustment, (for example, on a circular section) in particular on a semicircular section.

According to another advantageous embodiment of the invention, the measuring beam transmitter and the measuring beam receiver can be realized in the form of input openings and output openings of optical waveguides. Use of optical waveguides as receiving and transmitting components has the advantage that the structural size of the photometer can be further reduced. Moreover, more flexible adjusting and conducting of the measured intensity values through the optical waveguides in the interior of the photometer housing is provided.

According to another advantageous embodiment of the invention, the windows on the measuring slot of the photometer housing are provided with elastic holders, and drives for exciting the oscillation present on the windows. The oscillation can take place, for example, via piezoelectric ceramic material. An oscillation exciting of the windows has the advantage that it avoids depositing of dirt and particles present in the fluid to be examined. Expensive cleaning devices such as, for example, wipers or special nozzle jet devices are, therefore, not necessary. This ensures a permanent mode of operation even for a long time period of the photometer. An oscillation excitement can be, for example, in the range of 20 kHz to 120 kHz. Appropriate drives can be readily integrated into the interior of the housing. The use of a piezoceramic material has the advantage that a comparatively low energy input is required and cleaning is also ensured without wear for a long time period.

According to another advantageous embodiment of the invention, the measuring conduit is arranged in a previously determined, comparatively great distance from the reference conduit. The distance between the two conduits is preferably 2 cm to 4 cm. As a result of the great distance between the measuring conduit and the reference conduit, a reciprocal negative influence of the two repeated intensity value measurements is prevented. Screening elements can also be provided between the two conduits to prevent deflection of scattered light in the direction of the other one of the two conduits.

According to another advantageous embodiment of the invention, e means for detecting and evaluating intensity values of the measuring beam are integrated in the housing. According to one alternative embodiment in this regard, means for detecting and evaluating can also be present outside the housing in a separate structural part located outside the fluid.

According to another advantageous embodiment of the invention, the photometer housing has an oblong tubular shape and is constructed to be completely encapsulated. A complete encapsulation of the housing has the advantage that it is fluid-tight and secure against damage and penetration of elements from the outside. An encapsulated form of the housing is preferably provided with opening means for maintenance and repair of the photometer.

BRIEF DESCRIPTION OF THE DRAWINGS

Other advantages, features and details result from the following description in which exemplary embodiments are described in detail with reference made to the drawings. The features shown in the drawings and mentioned in the description may be essential for the invention individually, or in any combination.

In the drawings.

DETAILED DESCRIPTION OF THE PREFERRED EMBODIMENTS

Figure 1:
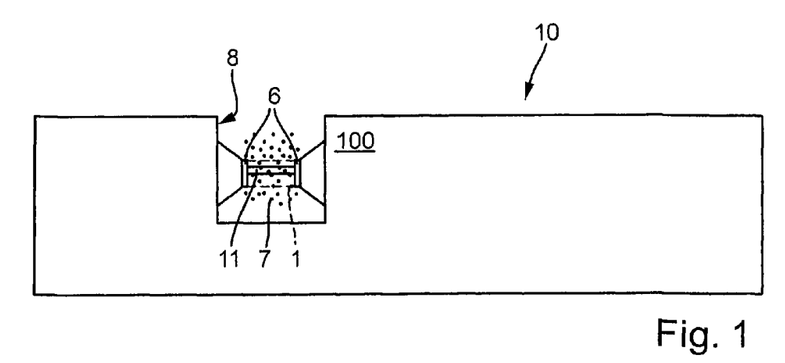
FIG. 1 shows a schematic side view of a first exemplary embodiment of a photometer, in accordance with the invention, for illustrating the outer shape.

FIG. 1 shows a schematic top view of a first exemplary embodiment of a photometer, in accordance with the invention, for the on-site measuring of substances in fluids. A tubular, oblong housing 100, that is in this exemplary embodiment approximately one third of the longitudinal extension of the housing 100, is provided with the housing slot 8 that is open to the fluid. The measuring slot 8 is provided here with a depth of approximately one half the diameter of the housing and has two measuring windows 6 on the opposite sides that are transparent for a measuring beam 11 from the interior of the housing 100 of the photometer 10. The housing 100 of the photometer 10 is constructed to be completely encapsulated, i.e., it is fluid-tight and suitable for being completely immersed into a liquid medium. The photometer 10 is provided with connection lines for the supplying of energy and for transmitting measured values to the outside from the liquid medium (not shown in FIG. 1). In the interior of the housing 100 the photometer 10 is equipped with a measuring beam transmitter 30 and a measuring beam receiver 31 (cf. FIG. 2, for example). Furthermore, the photometer 10 comprises, in accordance with this exemplary embodiment, a specifically movable carrier part in the interior of the housing 100 that is constructed in such a manner that a generated measuring beam 11 can be shifted from the position of the measuring conduit 1 between the two windows 6 in a measuring slot 7 to a reference conduit 51 that is different from the measuring conduit 1. The function and the construction of the interior of the photometer 10, in accordance with the invention, and the adjusting of the measuring beam 11 onto a given path B is explained in more detail in conjunction with the following figures. In the exemplary embodiment according to FIG. 1, the measuring windows 6 are mounted at a predetermined distance from one another in the measuring slot 7 on conically projecting sections so that the length of the measuring beam 11, i.e., the dimension between the two measuring windows 6, is less than that of the measuring slot 8 in the housing 100. The geometry and in particular the diameter of the measuring conduit 1, through which the measuring beam is conducted is preferably equal to that of a reference conduit that is located inside the housing 100 and to which the measuring beam 11 can be shifted by a carrier part that can move on a predetermined path B. The measuring windows 6 can alternatively also be mounted flush with the side walls of the measuring slot 8 in the housing 100. The measuring windows 6 are preferably elastically supported and provided with oscillation-producing elements such as, for example, electrically activatable piezoceramic materials.

Figure 2:
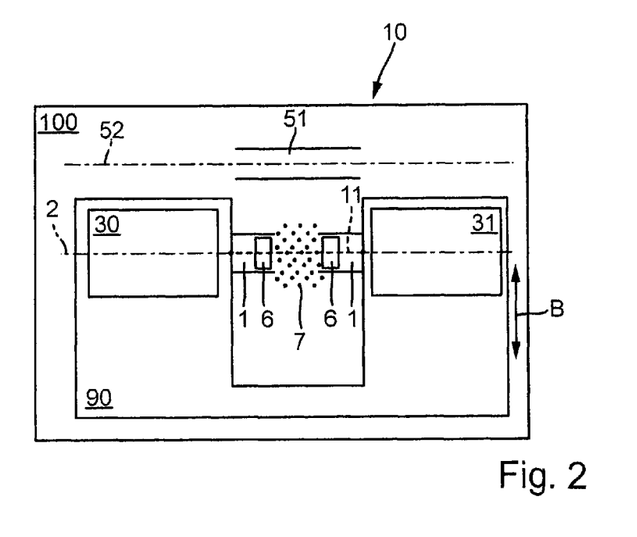
FIGS. 2 and 3 show schematic top views of a second exemplary embodiment of a photometer, in accordance with the invention, in measuring position and in referencing position.
Figure 3:
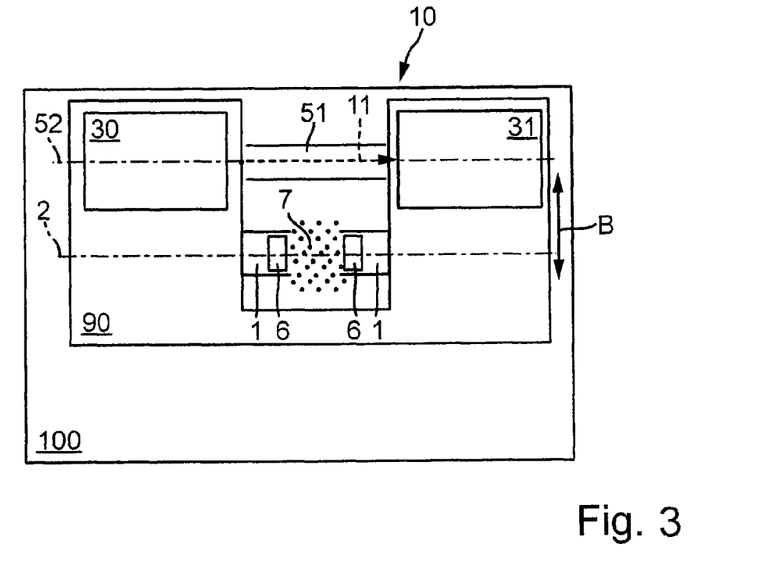

FIGS. 2 and 3 show in schematic top views the operation and the inner construction of the photometer 10, in accordance with an embodiment of the invention in different positions. Whereas the measuring conduit 1 is located in the area of the measuring slot 7 between the measuring windows 6 (cf. also FIG. 1), a reference conduit 51 arranged at a distance from it is formed in the interior of the housing 100. The reference conduit 51 is formed in such a manner that the measuring beam produced between the measuring beam transmitter 30 and the measuring beam receiver 31 can be adjusted, by shifting a carrier part 90, from the position of the measuring conduit 1 (cf. FIG. 2) into the position of the reference conduit 51 (cf. FIG. 3). In the exemplary embodiment of FIGS. 2 and 3, this changing of the measuring beam 11 takes place on a straight path B, as is illustrated with the movement arrow in FIGS. 2 and 3. Therefore, the measuring beam 11 is shifted in a type of parallel shifting from the measuring conduit 1, in which the measuring of particles of a substance is analyzed, for example, inside the fluid to be examined, into the position of a reference conduit 51. A referencing of the photometer 10 takes place in the reference conduit 51, whereby the same components and the same parameters are advantageously used as in the measuring in the measuring conduit 1. A linear shifting of the carrier part 90 and with it the measuring beam transmitter 30 and the measuring beam receiver 31 mounted on it can be realized with any means. For example, the linear shifting or parallel shifting is realized via mechanical tracks and guides, as well as by electrically operated actuators, or the like. The axis 2 of the measuring conduit is parallel to the axis 52 of the reference conduit so that a changing between the measuring position and the referencing position (cf. FIG. 3) takes place by a simple lateral shifting of the carrier part 90 along the path B. Furthermore, in this exemplary embodiment of the invention, detection means and evaluation means are provided in the housing 100 of the photometer 10 with which the intensity values of the measuring in the measuring conduit 1 and the values of the referencing in the reference conduit 51 can be detected and evaluated. As a result, the device is always ready for operation even in the case of an age-related change of the components. The measuring beam transmitter 30 can be a normal light or another light-emitting component such as, for example, a UV light, a laser light, or the like. The measuring beam receiver 31 also has a traditional form known to the person skilled in the art and is realized, for example, in the form of photodiodes or other electronic, photosensitive structural components. The wavelength of the measuring beam can be adjusted according to the constituents in a fluid to be measured. Thus, for example, a nitrate content or a content of other organic substances in wastewater or in sea water can be examined with the sound of the photometer 10.

Figure 4:
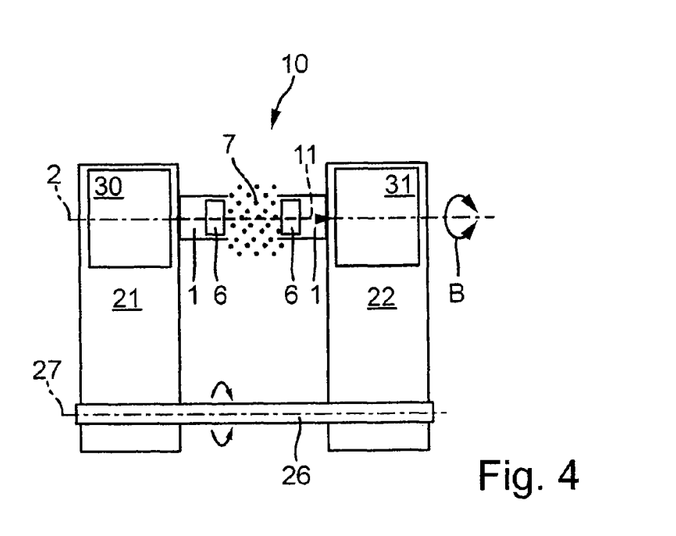
FIGS. 4 and 5 show schematic top views of a third exemplary embodiment of a photometer, in accordance with the invention, in measuring position and in referencing position.
Figure 5:
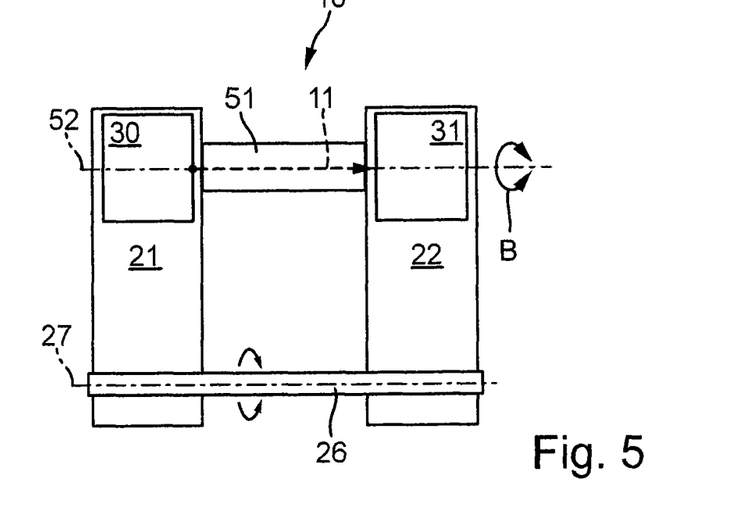

FIGS. 4 and 5 show another exemplary embodiment of a photometer 10, in accordance with the invention in different schematic positions. For reasons of simplification, the housing 100 of the photometer 10 is no longer shown in these figures and in the following figures. However, it has a similar form and design as in the previous exemplary embodiments and in particular is equipped with a defined measuring slot 7 and opposing windows 6 that make possible a measurement by a measuring beam 11 in the fluid itself, i.e., on site, with immersed photometer 10 (so-called "in-situ measuring"). In the exemplary embodiment, according to FIGS. 4 and 5, the carrier part 21, 22 is no longer adjusted on a linear, predetermined path B, but rather on a circular path B. To this end, the measuring beam transmitter and the measuring beam receiver 31 are each mounted on a separate carrier part 21, 22. The two carrier parts 21, 22 are rigidly connected to a rotatable shaft 26. As a result, the measuring beam transmitter 30 and the measuring beam receiver 31 are shifted around the axis of rotation 27 of the shaft 26 on a common circular path B, as is indicated in the figures with the arrow of rotation B. The shifting along the given path also takes place, in accordance with the invention, for switching between an actual measurement with the measuring beam 11 in a measuring conduit 1 (FIG. 4) that is located in the area of a measuring slot 7 on the outside of the housing 100 (not shown) and between a reference conduit 51 that is separate from it, (i.e., positioned at another location, as illustrated in FIG. 5). The rotational shifting along the circular path B has the advantage that a comparatively large distance between the reference conduit 51 and the measuring conduit 1 is made possible in a relatively small structural space. Furthermore, no additional mechanical structural elements such as guide rails or cogged rods, etc., are necessary for carrying out the changing of the measuring beam 11 from the referencing position into the measuring position. A simple, rotatable shaft 26 that can be driven by an appropriate electrical motor or the like is sufficient for realizing the referencing, in accordance with the invention. Even in the exemplary embodiment of FIGS. 4 and 5, appropriate detection means and evaluation means for the intensity values are present, on the one hand, in the reference conduit 51 and, on the other hand, in the measuring conduit 1. The detection, evaluation and storing of the measured values, as well as their display, takes place in a manner known to the person skilled in the art.

Figure 6:
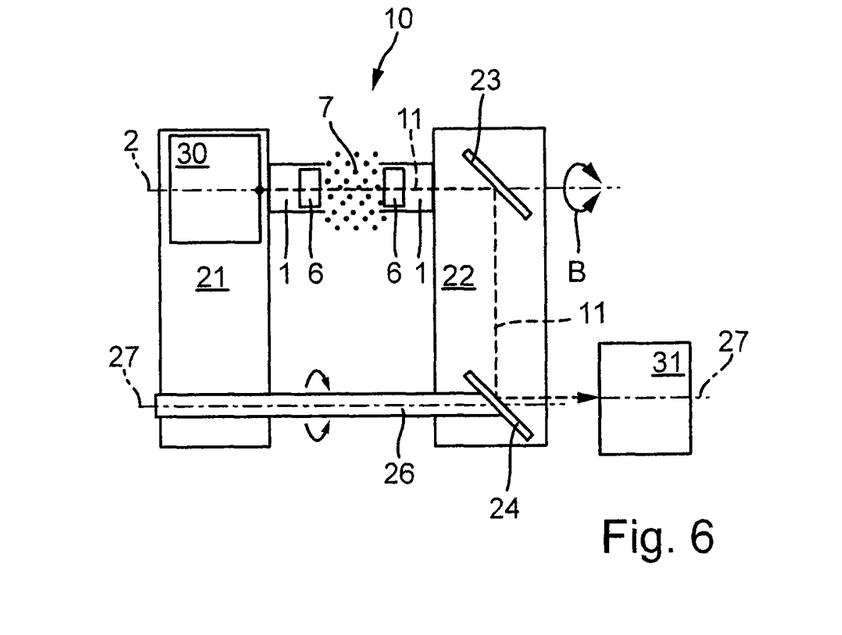
FIG. 6 shows a schematic top view of a fourth exemplary embodiment of a photometer, in accordance with the invention.

Even in a further exemplary embodiment of a photometer 10, in accordance with the invention and according to FIG. 6, the changing of the at least one carrier part inside the housing 100 (not shown) takes place by a circular movement B, i.e., a movement on a segment of a circle, preferably in an angular range of 30° to 90°. However, in distinction to the previous exemplary embodiment, only the measuring beam transmitter 30 is mounted on a carrier part 21 that can move in a rotary movement. The measuring beam receiver 31, on the other hand, is permanently mounted in the housing 100 of the photometer 10 with its central axis in the axis of rotation 27 of the shaft 26. The rotation of the shaft 26 about the axis of rotation 27, nevertheless, produces a shifting of the measuring beam 11 from the measuring position in the measuring conduit 1 shown in FIG. 6 into the reference conduit 51 (not shown) in accordance with the given circular movement path B (cf. movement arrow B in FIG. 6). The measuring beam 11 transmitted from the measuring beam transmitter 30 through the measuring window 6, as is indicated with the dotted line in FIG. 6, is taken up again in the interior of the housing by the opposing measuring window 6 and diverted via two mirrors 23, 24 that are permanently mounted on a second carrier part 22, into the central axis of the measuring beam receiver 31. Since the measuring beam receiver 31 is located in the axis of rotation 27 of the shaft 26, it can also be permanently mounted according to this embodiment of the invention inside the housing 100. This has advantages in that the sensitive optical structural components of the measuring beam receiver 31 are not exposed to any unnecessary agitation and the connection cables and the signal lines are simplified. This improves the operational safety and ensures a long-term operating time of the photometer 10.

Figure 7:
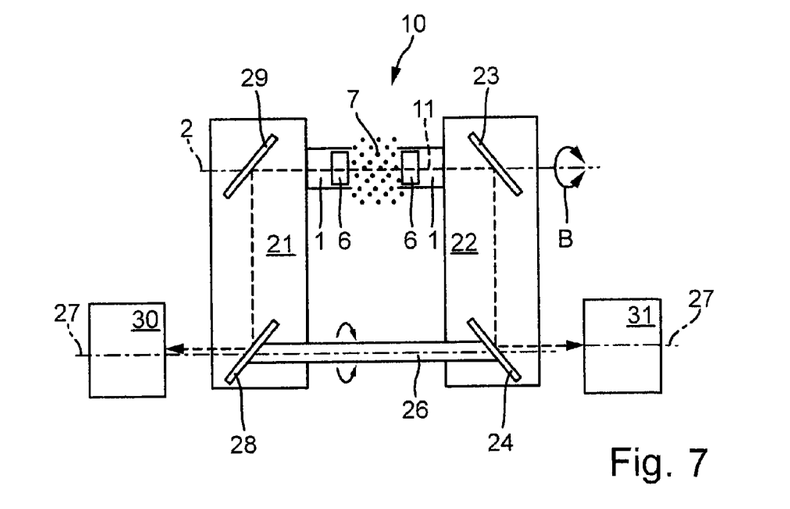
FIG. 7 shows a schematic top view of a fifth exemplary embodiment of a photometer, in accordance with the invention.

According to the further exemplary embodiment in accordance with FIG. 7, a construction similar to the previous two exemplary embodiments is provided inside the housing 10 of the photometer. The two carrier parts 21, 22 can be shifted according to a given circular path B by a shaft 26 that is rigidly connected to them. The shaft 26 rotates about an axis of rotation 27, whereby optical deflection means such as, for example, mirrors 23, 24, 28, 29 are mounted on the carrier parts 21, 22 so that the measuring beam 11 produced between the measuring beam transmitter 30 and the measuring beam receiver 31 can be shifted, in accordance with the invention. The mirrors 23, 24, 28, 29 are mounted at a 45° angle at the location of the axis of rotation 27 of the shaft 26 and on the opposing free end of the carrier parts 21, 22 at the level of the measuring conduit 1. A reference conduit 51 (not shown in FIG. 7) is present at an appropriate position at a distance from the shaft 26, so that a rotary shifting of the shaft 26 along the path B takes place with a changing of the measuring beam 11 between the free ends of the carrier parts 21, 22 into a position of the reference conduit 51 for the referencing of the photometer 10. In this exemplary embodiment according to FIG. 7, the measuring beam transmitter 30, as well as the measuring beam receiver 31, can be permanently mounted inside the housing since they are both positioned with their central axes at the axis of rotation 27 of the shaft 26, so that a deflection of the measuring beam 11 onto the two desired positions, on the one hand, that of the measuring conduit 1 between the measuring windows 6 in the measuring slot 7 of the housing and, on the other hand, that of the reference conduit 51, is possible with relatively simple optical means (four mirrors in this example). The rotary movement of the shaft 26 can take place by suitable means, for example, an electromotor. Here too, appropriate evaluation means and detection means for the detection, evaluation and storing of the measured intensity values are present inside the housing 100 (not shown) of the photometer 10. The photometer 10 is preferably also constructed in a completely encapsulated structural form of an outer housing 100 so that immersion into the liquid medium to be analyzed is made possible.

Figure 8:
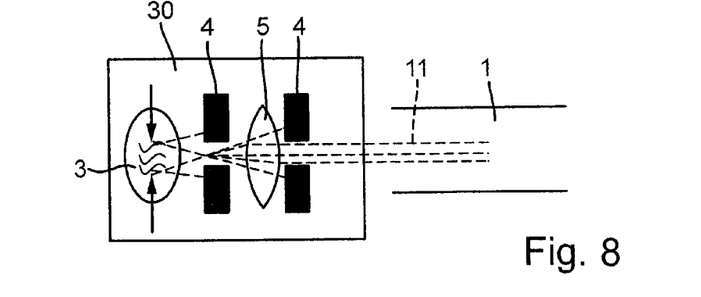
FIG. 8 shows a schematic detailed view of an embodiment of the measuring beam transmitter for the photometer in accordance with the invention.
Figure 9:
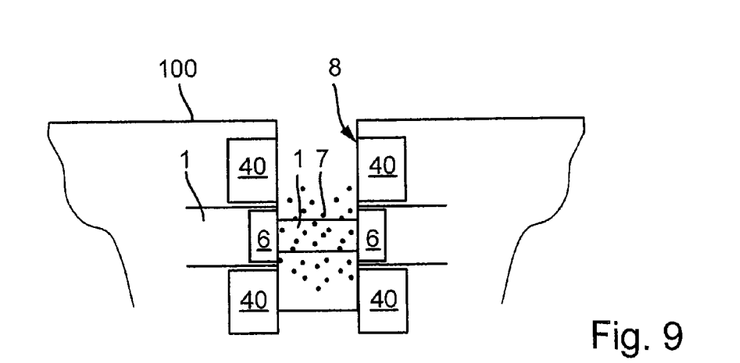
FIG. 9 shows a schematic detailed view of an embodiment of the invention including the windows with oscillation drives.

FIGS. 8 and 9 show detailed views, on the one hand, of a possible construction of a measuring beam transmitter 30 and, on the other hand, of the measuring windows 6 for a photometer 10, in accordance with the invention. FIG. 8 shows a possible embodiment of a measuring beam transmitter 30, in which a measuring beam 11 is generated with a predetermined form that, according to the invention, preferably has a smaller diameter that the measuring conduit 1, or the reference conduit 51 (for example, ¾ of the diameter of the conduits 1, 51). The measuring beam transmitter 30 is formed by a lamp 3 positioned behind a diaphragm 4 and a lens 5, for example, in the form of a lens for the 1 bundling of the measuring beam 11. A second diaphragm 4 is present behind the lens 5, so that an approximately parallel measuring beam 11 with a predetermined diameter exits from the measuring beam transmitter 30.

In the example according to FIG. 9, the measuring windows 6 are not rigidly built at opposite positions of the measuring slot 7 in the housing 100 of the photometer 10, but rather are supported flexibly, i.e., with elastic means, or the like. The measuring windows 6 are furthermore provided on both sides of the measuring conduit 1 with drives 40 of a device for generating oscillations so that the windows 6 can be put in a permanent or periodic oscillation. The generation of oscillations on the windows 6 has the advantage that a deposition of dirt particles or of organic substance or plants on the outside is prevented. A repeated cleaning outside of the medium for the maintaining of the correct operation of the photometer 10 is therefore not necessary. The devices for generating oscillations with the drives 40 can be constructed, for example, in the form of piezoelectric ceramic materials so that a generation of oscillations at the windows 6 is made possible with a comparably low consumption of energy.

Other forms of devices for the generation of oscillations can also be used in accordance with the invention. Examples for such oscillation generators are also described and disclosed in DE 198 of 11 876 A1 from the same applicant, that is expressly included here by way of reference in this regard. The device for the generation of oscillations of the windows 6 is preferably designed in such a manner that oscillations in a frequency range of 20 kHz to 120 kHz can be produced. Expensive cleaning devices or repeated maintenance work for cleaning the outside, especially the windows of the photometer 10 can be avoided in this manner. The invention is not limited to the described exemplary embodiments and comprises all modifications and embodiments falling within the protected range of the following claims. In particular, the photometer in accordance with the invention is not limited to a usage of an on-site measuring in a liquid medium and can also be used in a corresponding manner in gaseous media. The outer form of the housing 100 can have another shape instead of a tubular form, as is shown in FIG. 1, so long as a measuring slot 7 that is accessible for the medium to be measured is present. The changing of the measuring beam from the referencing position into the position of the measuring conduit can take place with other means than those described.

The invention claimed is:

1. A photometer (10) for measuring photometric magnitudes in a liquid medium, comprising a housing (100) adapted to be introduced into the medium for on-site measurement; a light-emitting measuring beam transmitter (30) and a measuring beam receiver (31) arranged behind opposing measuring windows (6) on a measuring slot in the housing (100), in which the slot is open to the medium, wherein a measuring beam (11) is generated in a measuring conduit (1) disposed in the measuring slot (7) with at least one predetermined wavelength for measuring light absorption in the medium; a reference conduit (51) for a reference measurement, which is separate from the measuring conduit (1), disposed in the housing (100); at least one carrier part (90, 21, 22) including the measuring beam transmitter (30), the measuring beam receiver (31) and their optical structural components, in which the one carrier part is configured to move on a path (B) in the housing (100) from the measuring conduit (1) to the reference conduit (51) and back, for measuring intensity values of the measuring beam (11) in the measuring conduit (1) and in the reference conduit (51); and means for detecting and evaluating the measured intensity values;

wherein the measuring conduit is completely immersed within the liquid medium upon the liquid medium entering the measuring slot; and the measuring beam is generated toward both, the measuring conduit and the measuring slot.

2. The photometer according to claim 1, wherein the measuring beam transmitter (30) and the measuring beam receiver (31) are mounted on a common carrier part (90) that is configured to move on a linear path (B) in the housing (100) for adjusting the measuring beam (11).

3. The photometer according to claim 1, wherein the measuring beam (11) is configured to be adjusted on a circular path (B) between the measuring conduit (1) and the reference conduit (51).

4. The photometer according to claim 1, wherein the measuring conduit (1) and the reference conduit (51) have substantially the same geometry, including the same cross section and the same length.

5. The photometer according to claim 1, wherein measuring the intensity values are obtained in the measuring conduit (1) and in the reference conduit (51) with identical parameters and components.

6. The photometer according to claim 1, wherein, the cross section of the measuring beam (11) is smaller than the cross section of the measuring conduit (1) or the reference conduit (51).

7. The photometer according to claim 6, wherein, the measuring beam (11) emitted by the measuring beam transmitter (30) is defined by optical elements, including a diaphragm (4) and a lens (5).

8. The photometer according to claim 1, wherein the measuring beam transmitter (30) is mounted on a first carrier part (21) and the measuring beam receiver (31) is mounted on a second carrier part (22), and the carrier parts (21, 22) are rigidly connected to a shaft (26) that is configured to rotate about an axis of rotation (27).

9. The photometer according to claim 1 wherein the measuring beam transmitter (30) is mounted on a carrier part (21) that is rigidly connected to a shaft (26) that rotates about an axis of rotation (27), the measuring beam receiver (31) includes a central axis in the axis of rotation (27), and means (23, 24) are provided for deflecting the measuring beam (11).

10. The photometer according to claim 1, wherein the measuring beam transmitter (30) and the measuring beam receiver (31) are arranged with their respective central axis in the axis of rotation (27) of a rotatable shaft (26) that is rigidly connected to the one carrier part (21, 22), and the one carrier part (21, 22) includes optical means (23, 24, 29, 28) for deflecting the measuring beam (11).

11. The photometer according to claim 1, wherein the one carrier part (90) has a substantially U-shaped form with a U-shaped inner slot suitable for receiving the measuring slot (7) which is open to the liquid medium, and the measuring conduit is immersed in the liquid medium upon the U-shaped inner slot receiving the liquid medium.

12. The photometer according to claim 1 wherein the measuring beam transmitter (30) and the measuring beam receiver (31) include input openings and output openings of optical waveguides.

13. The photometer according to claim 1, wherein the windows (6) on the measuring slot (7) are provided with elastic holders and drives (40) for exciting oscillation.

14. The photometer according to claim 1, wherein the measuring conduit (1) is positioned at a predetermined distance from the reference conduit (51), preferably between 2 cm to 4 cm.

15. The photometer according to claim 1, wherein the means for detecting and evaluating the intensity values of the measuring beam (11) are integrated in the housing (100).

16. The photometer according to claim 1, wherein the housing (100) has an oblong tubular shape and is completely encapsulated.

* * * * *

UNITED STATES PATENT AND TRADEMARK OFFICE
CERTIFICATE OF CORRECTION

PATENT NO. : 8,902,427 B2
APPLICATION NO. : 13/467350
DATED : December 2, 2014
INVENTOR(S) : Michael Holeczek et al.

Page 1 of 1

It is certified that error appears in the above-identified patent and that said Letters Patent is hereby corrected as shown below:

ON TITLE PAGE, ITEM (73) ASSIGNEE: "WTW Wissenschaflich-Technische Werstatten GmbH"

SHOULD READ -- WTW Wissenschaftlich-Technische Werkstätten GmbH --.

Signed and Sealed this
Thirty-first Day of March, 2015

Michelle K. Lee
*Director of the United States Patent and Trademark Office*